United States Patent
Gröning et al.

(12)

(10) Patent No.: US 6,258,959 B1
(45) Date of Patent: Jul. 10, 2001

(54) PROCESS FOR THE PREPARATION OF 2,4-DIMETHYL-3,5-BISALKOXYCARBONYLPYRROLE

(75) Inventors: Carsten Gröning, Mannheim; Reinhard Kemper, Heidelberg; Markus Frede, Eppelheim; Klaus Ebel, Lampertheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/459,724

(22) Filed: Dec. 13, 1999

(30) Foreign Application Priority Data

Dec. 17, 1998 (DE) .............................. 198 58 352

(51) Int. Cl.[7] .............................. C07D 207/416
(52) U.S. Cl. .............................. 548/533
(58) Field of Search .............................. 548/533

(56) References Cited

FOREIGN PATENT DOCUMENTS 078545   5/1983   (EP) .
170214   2/1986   (EP) .

OTHER PUBLICATIONS

Jones et al. (Pyrrole Studies) A Critical Evaluation of the Knorr Synthesis of trifluoromethylpyrroles Synth. Commun. (1984) 14 (6), pp. 575–578.*
Treibs et al., *Chem. Ber.*, 90, 1957, 79–90.
*Org. Synth. Coll.*, vol. II, 1943, 202–204.

* cited by examiner

*Primary Examiner*—Floyd D. Higel
*Assistant Examiner*—Ebenezer Sackey
(74) *Attorney, Agent, or Firm*—Keil & Weinkauf

(57) ABSTRACT

A process for the preparation of 2,4-dimethyl-3,5-bisalkoxycarbonylpyrrole is described, in which an acetoacetic alkyl ester is nitrosated to give the 2-nitrosoacetoacetic alkyl ester, the nitroso compound is reduced using hydrogen in the presence of a noble metal catalyst to give the amine, and the resulting amino compound is condensed without isolation in the presence of the corresponding non-nitrosated acetoacetic alkyl ester to give the 2,4-dimethyl-3,5-bisalkoxycarbonylpyrrole. The process makes it possible to work under conditions which are milder than in the prior art and to avoid the formation of by-products.

6 Claims, No Drawings

PROCESS FOR THE PREPARATION OF 2,4-DIMETHYL-3,5-BISALKOXYCARBONYLPYRROLE

The invention relates to a process for the preparation of 2,4-dimethyl-3,5-bisalkoxycarbonylpyrrole in which an acetoacetic alkyl ester is nitrosated in the 2-position, reduced to give the amino compound and then condensed to give the 2,4-dimethyl-3,5-bisalkoxycarbonylpyrrole.

As well as having other possible uses, this compound is a useful intermediate in the synthesis of 2,4-dimethylpyrrole, which is obtained from the dicarboxylic ester in a known manner by hydrolysis and decarboxylation.

The synthesis of 2,4-dimethyl-3,5-bisethoxycarbonylpyrrole is described in Org. Syntheses, Coll. Vol. II, 202–204 (1943). The reducing agent used for the nitroso group is elemental zinc. The yield is at most 64%. Treibs et al. describe the reduction of the nitroso compound using sodium disulfate (III) (sodium dithionite) in Chem. Ber. 90, 79 (1957) in 85% yield.

Both reducing agents have technological disadvantages. Zinc, being a solid, can only be handled on an industrial scale at relatively high cost. To dispose of the zinc-salt-containing solutions which are produced in an environmentally responsible manner, or to process them further incurs considerable costs. The use of sodium dithionite also produces an increased salt content and is undesired from an environmental point of view.

EP-A 170 214 and 078 545 disclose the hydrogenation of nitrosated 1,3-diketones and of nitrosated β-ketocarboxylate esters respectively with hydrogen in the presence of a palladium catalyst to give the corresponding amines. Isolating a 2-nitrosoacetoacetic ester and then hydrogenating in this manner gives, essentially by condensation of two molecules of the amino compound to the six-membered ring, the 2,5-dimethyl-3,6-bisalkoxycarbonyl dihydropyrazine or its hydrogenation products. Condensation of the amino compound with an unsubstituted acetoacetic ester to give the pyrrole derivative is therefore no longer possible.

It is an object of the present invention to propose a process for the preparation of 2,4-dimethyl-3,5-bisalkoxycarbonylpyrrole which produces the product in high yield and in which the by-products which form can be disposed of without problem.

We have found that this object is achieved by a process for the preparation of 2,4-dimethyl-3,5-bisalkoxycarbonylpyrrole, in which an acetoacetic alkyl ester is nitrosated to give the 2-nitrosoacetoacetic alkyl ester, the nitroso compound is reduced to give the amine, and the amine, together with unsubstituted acetoacetic alkyl ester, is condensed with ring closure to give the 2,4-dimethyl-3,5-bisalkoxycarbonylpyrrole.

The process according to the invention comprises hydrogenating the nitroso compound with hydrogen in the presence of a noble metal catalyst, and condensing the resulting amino compound without isolation in the presence of the corresponding non-nitrosated acetoacetic alkyl ester to give the 2,4-dimethyl-3,5-bisalkoxycarbonylpyrrole.

The synthesis proceeds according to the following equations

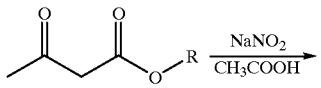

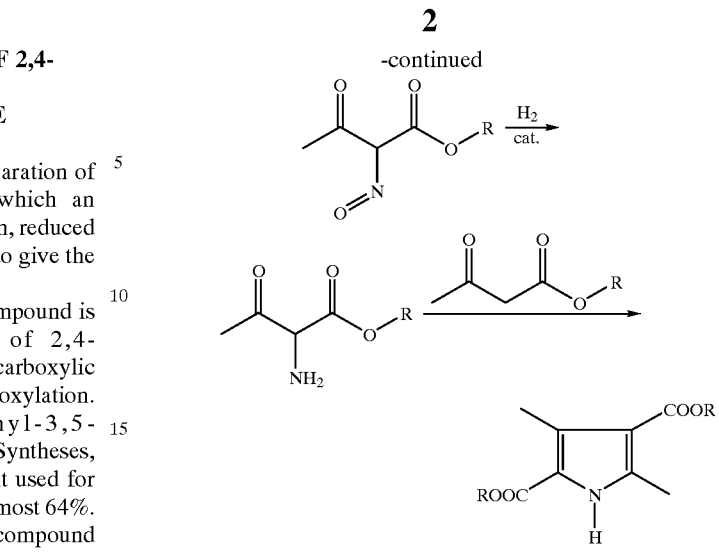

R is an alkyl group having from 1 to 4 carbon atoms and is preferably methyl of ethyl.

The noble metal catalyst can be a metal from the platinum group, for example palladium or platinum, on a support having a large surface area, for example activated carbon.

Surprisingly, we have now found that the desired pyrrole derivative is obtained directly without isolation of the nitroso compound by hydrogenation of the nitrosated crude solution in the presence of excess acetoacetic alkyl ester.

It is therefore essential for the synthesis that the nitrosation is carried out with a deficit, i.e. from about 10 to 50%, preferably from 20 to 40% of the stochiometric amount, of sodium nitrite. The nitrosation with sodium nitrite and acetic acid in aqueous solution is usually carried out with cooling to a temperature between 0° C. and room temperature, preferably below 15° C.

The catalytic hydrogenation is normally carried out at slightly elevated temperature, for example in the range from above room temperature to 60° C., and under a hydrogen pressure of from 5 to 20 bar. The resulting 2,4-dimethyl-3,5-bisalkoxycarbonylpyrrole precipitates out of the solution and can be filtered off.

The examples below illustrate the advantages of the process according to the invention. Unless stated otherwise, parts and percentages are in units by weight.

EXAMPLE 1
(Comparative Example)

A solution of 70 g of methyl acetoacetate (0.60 mmol) in 100 g of acetic acid was nitrosated at from 5 to 10° C. with a solution of 50 g of sodium nitrite (0.72 mol) in 75 g of water. The excess nitrous acid was destroyed using urea; completion of the reaction was checked using potassium iodide starch paper. The solution was extracted with ether, the extract was washed with sodium carbonate solution and water, and the ether was distilled off under reduced pressure, giving 30.8 g of a yellow oil.

10 g of the resulting oil were hydrogenated with 2 g of Pd/activated carbon (5% Pd) in 100 ml of acetic acid at 50° C. under 9 bar of hydrogen pressure. The solid sediment was filtered off, and the filtrate was heated to boiling with 20 g of methyl acetoacetate. The filtrate was neutralized with sodium carbonate solution. The desired 2,4-dimethyl-3,5-bismethoxycarbonylpyrrole did not precipitate out. The solution was extracted with ether and analyzed by gas chromatography. Only the 2,5-dimethyl-3,6- bismethoxycarbonyldihydropyrazine or its hydrogenation products were detected.

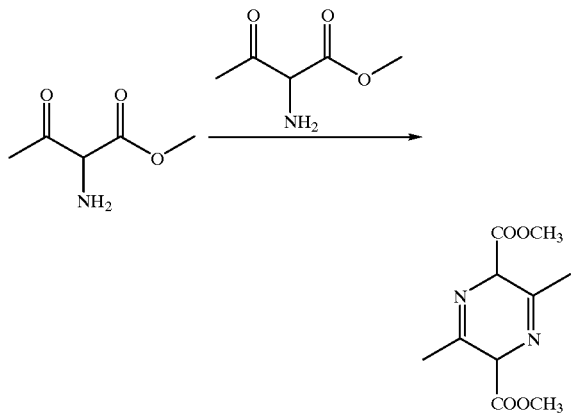

EXAMPLE 2

375 g of a 40% strength aqueous sodium nitrite solution (2.17 mol) were metered, at from 5 to 10° C., into a mixture of 281 g of acetic acid and 984 g of methyl acetoacetate (8.48 mol) over 3 hours with stirring and cooling. The reaction mixture was stirred for a further 5 hours with cooling and then allowed to warm to room temperature. 4.7 g of palladium/activated carbon (5% Pd) were added to the clear solution, which was hydrogenated at 40° C. under a hydrogen pressure of from 9 to 10 bar until no more hydrogen was absorbed (about 24 hours). 300 g of water were added to the resulting suspension to complete precipitation, and the suspension was filtered, giving 399 g of catalyst-containing filter residue (1.89 mol of 2,4-dimethyl-3,5-bismethoxycarbonylpyrrole; yield: 87% based on sodium nitrite; 45% based on methyl acetoacetate).

We claim:

1. A process for the preparation of 2,4-dimethyl-3,5-bisalkoxycarbonylpyrrole, in which an acetoacetic alkyl ester is nitrosated to give the 2-nitrosoacetoacetic alkyl ester, the nitroso compound is reduced to give the amine, and the amine, together with unsubstituted acetoacetic alkyl ester, is condensed with ring closure to give the 2,4-dimethyl-3,5-bisalkoxycarbonyl-pyrrole, which comprises hydrogenating the nitroso compound with hydrogen in the presence of a noble metal catalyst, and condensing the resulting amino compound without isolation in the presence of the corresponding non-nitrosated acetoacetic alkyl ester to give the 2,4-dimethyl-3,5-bisalkoxycarbonylpyrrole.

2. A process as claimed in claim 1, wherein the acetoacetic alkyl ester is nitrosated with from 10 to 50% of the stochiometric amount of nitrous acid, and the resulting partially nitrosated mixture is subjected directly to condensation.

3. A process as claimed in claim 1, wherein the acetoacetic alkyl ester has from 1 to 4 carbon atoms in the alkyl group.

4. A process as claimed in claim 1, wherein the noble metal is a metal from the platinum group.

5. A process as claimed in claim 1, wherein the catalytic hydrogenation is carried out at a temperature between room temperature and 60° C.

6. A process as claimed in claim 1, wherein the catalytic hydrogenation is carried out under a pressure of from 5 to 20 bar.

* * * * *